United States Patent
Edwards et al.

(10) Patent No.: US 10,111,673 B2
(45) Date of Patent: Oct. 30, 2018

(54) POLYMER 4-IN-1 FEMORAL CUTTING BLOCK INCLUDING METALLIC PROTECTIVE BUSHINGS

(71) Applicant: DEPUY SYNTHES PRODUCTS, INC., Raynham, MA (US)

(72) Inventors: Jon M. Edwards, Warsaw, IN (US); Michael J. Rock, Leeds (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 1407 days.

(21) Appl. No.: 13/785,287

(22) Filed: Mar. 5, 2013

(65) Prior Publication Data
US 2014/0257306 A1    Sep. 11, 2014

(51) Int. Cl.
*A61B 17/58* (2006.01)
*A61B 17/90* (2006.01)
*A61B 17/15* (2006.01)
*A61B 17/00* (2006.01)

(52) U.S. Cl.
CPC .. *A61B 17/155* (2013.01); *A61B 2017/00831* (2013.01)

(58) Field of Classification Search
CPC ..... A61B 17/154; A61B 17/155; A61B 17/15; A61B 17/151; A61B 2017/0023
USPC ..................................................... 606/87–89
See application file for complete search history.

(56) References Cited

U.S. PATENT DOCUMENTS

| | | |
|---|---|---|
| 5,129,909 A | 7/1992 | Sutherland |
| 5,178,621 A | 1/1993 | Cook |
| 5,403,321 A | 4/1995 | DiMarco |
| 5,683,397 A | 11/1997 | Vendrely |
| 5,716,361 A | 2/1998 | Masini |
| 7,967,824 B2 | 6/2011 | Thau et al. |
| 2003/0018338 A1 | 1/2003 | Axelson, Jr. et al. |
| 2005/0209605 A1* | 9/2005 | Grimm et al. ................. 606/96 |
| 2005/0228393 A1 | 10/2005 | Williams, III et al. |
| 2007/0213738 A1 | 9/2007 | Martin |
| 2008/0154269 A1 | 6/2008 | Roger et al. |
| 2008/0221569 A1 | 9/2008 | Moore |
| 2009/0222014 A1 | 9/2009 | Bojarski |
| 2010/0168752 A1* | 7/2010 | Edwards ........................ 606/87 |
| 2010/0168753 A1 | 7/2010 | Edwards et al. |
| 2010/0191244 A1 | 7/2010 | White |
| 2013/0325017 A1 | 12/2013 | Lomicka |

(Continued)

FOREIGN PATENT DOCUMENTS

| | | |
|---|---|---|
| EP | 2039304 A2 | 3/2009 |
| EP | 2208469 A1 | 7/2010 |
| EP | 2319433 A1 | 5/2011 |

(Continued)

OTHER PUBLICATIONS

European Search Report for European Application No. 14157968.0-1654, dated May 15, 2014, 5 pages.

(Continued)

*Primary Examiner* — Zade Coley
*Assistant Examiner* — Jessica Weiss
(74) *Attorney, Agent, or Firm* — Barnes & Thornburg LLP (57) ABSTRACT

An orthopedic surgical instrument includes a polymer 4-in-1 cutting block having a number of metallic cutting guides secured thereto. A pair of metallic bushings function as saw stops at the medial and lateral ends of the chamfer cutting slot.

19 Claims, 5 Drawing Sheets

(56) References Cited

U.S. PATENT DOCUMENTS

2014/0257305 A1    9/2014   Edwards

FOREIGN PATENT DOCUMENTS

| JP | 2005253970 A | 9/2005 |
| JP | 2010158519 A | 7/2010 |
| WO | 2012024317 A2 | 2/2012 |

OTHER PUBLICATIONS

Australian Examination Report No. 1 for Australian Application No. 2014201030 dated Dec. 9, 2017, 4 pages.
Japanese Seach/Examination Report for Japanese Patent Application No. 2014-041288 dated Dec. 19, 2017, 6 pages.
SIGMA Fixed Bearing Surgical Technique by DePuy Orthopaedics, Inc. (2010).

* cited by examiner

POLYMER 4-IN-1 FEMORAL CUTTING BLOCK INCLUDING METALLIC PROTECTIVE BUSHINGS

TECHNICAL FIELD

The present disclosure relates generally to orthopaedic surgical instruments and, more particularly, to surgical instruments used to resect a patient's bone.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. To facilitate the replacement of the natural joint with the prosthesis, orthopaedic surgeons use a variety of orthopaedic surgical instruments such as, for example, saws, drills, reamers, rasps, broaches, cutting blocks, drill guides, milling guides, and other surgical instruments.

SUMMARY

According to one aspect of the disclosure, an orthopaedic surgical instrument includes a polymer 4-in-1 femoral cutting block having a chamfer cutting slot defined therein. A first metallic planar cutting guide is secured within the chamfer cutting slot of the polymer 4-in-1 femoral cutting block. A second metallic planar cutting guide is also secured within the chamfer cutting slot of the polymer 4-in-1 femoral cutting block. The second metallic planar cutting guide is arranged at an oblique angle relative to, and spaced apart from, the first metallic planar cutting guide. A first metallic bushing is secured within the chamfer cutting slot of the polymer 4-in-1 femoral cutting block, with an outer surface of the first metallic bushing being positioned at a lateral end of each of the first and second metallic planar cutting guides. A second metallic bushing is also secured within the chamfer cutting slot of the polymer 4-in-1 femoral cutting block, with the outer surface of the second metallic bushing being positioned at a medial end of each of the first and second metallic planar cutting guides.

The outer surface of the first metallic bushing may be spaced apart laterally from the lateral end of each of the first and second metallic planar cutting guides, or may be positioned in contact with the lateral end of each of the first and second metallic planar cutting guides. Likewise, the outer surface of the second metallic bushing may be spaced apart medially from the medial end of each of the first and second metallic planar cutting guides, or positioned in contact with the medial end of each of the first and second metallic planar cutting guides.

Each of the first and second metallic bushings may be embodied as cylindrically-shaped bushings having an elongated bore extending therethrough.

In an embodiment, the second metallic planar cutting guide is spaced apart from the first metallic planar cutting guide in the anterior/posterior direction.

The orthopaedic surgical instrument may also include a third metallic planar cutting guide secured within the chamfer cutting slot of the polymer 4-in-1 femoral cutting block, and a fourth metallic planar cutting guide secured within the chamfer cutting slot of the polymer 4-in-1 femoral cutting block. The fourth metallic planar cutting guide may be arranged at an oblique angle relative to the third metallic planar cutting guide.

The polymer 4-in-1 femoral cutting block may also have an anterior cutting slot defined therein. The anterior cutting slot is spaced apart anteriorly from the chamfer cutting slot, and has a metallic anterior cutting guide secured within it.

Moreover, the polymer 4-in-1 femoral cutting block may also have a posterior cut surface defined therein. The posterior cut surface is spaced apart posteriorly from the chamfer cutting slot, and has a metallic posterior cutting guide secured to it.

According to another aspect, an orthopaedic surgical instrument includes a polymer 4-in-1 femoral cutting block having a chamfer cutting slot defined therein, and a metallic captured chamfer cutting guide assembly secured within the chamfer cutting slot. The metallic captured chamfer cutting guide assembly includes a first metallic planar cutting guide and a second metallic planar cutting guide arranged at an oblique angle relative to, and spaced apart from, the first metallic planar cutting guide. The metallic captured chamfer cutting guide assembly also includes a first metallic bushing having its outer surface positioned at a lateral end of each of the first and second metallic planar cutting guides, and a second metallic bushing having its outer surface positioned at a medial end of each of the first and second metallic planar cutting guides.

The outer surface of the first metallic bushing may be spaced apart laterally from the lateral end of each of the first and second metallic planar cutting guides, or may be positioned in contact with the lateral end of each of the first and second metallic planar cutting guides. Likewise, the outer surface of the second metallic bushing may be spaced apart medially from the medial end of each of the first and second metallic planar cutting guides, or positioned in contact with the medial end of each of the first and second metallic planar cutting guides.

Each of the first and second metallic bushings may be embodied as cylindrically-shaped bushings having an elongated bore extending therethrough.

In an embodiment, the second metallic planar cutting guide is spaced apart from the first metallic planar cutting guide in the anterior/posterior direction.

The orthopaedic surgical instrument may also include a third metallic planar cutting guide secured within the chamfer cutting slot of the polymer 4-in-1 femoral cutting block, and a fourth metallic planar cutting guide secured within the chamfer cutting slot of the polymer 4-in-1 femoral cutting block. The fourth metallic planar cutting guide may be arranged at an oblique angle relative to the third metallic planar cutting guide.

The polymer 4-in-1 femoral cutting block may also have an anterior cutting slot defined therein. The anterior cutting slot is spaced apart anteriorly from the chamfer cutting slot, and has a metallic anterior cutting guide secured within it.

Moreover, the polymer 4-in-1 femoral cutting block may also have a posterior cut surface defined therein. The posterior cut surface is spaced apart posteriorly from the chamfer cutting slot, and has a metallic posterior cutting guide secured to it.

According to another aspect, an orthopaedic surgical instrument includes a polymer cutting block having a cutting slot defined therein, and a metallic captured cutting guide assembly secured within the cutting slot. The captured metallic chamfer cutting guide assembly may include a first metallic planar cutting guide, and a second metallic planar cutting guide spaced apart from the first metallic planar cutting guide. The captured metallic chamfer cutting guide assembly may also include a first metallic bushing having an outer surface thereof positioned at a first end of each of the first and second metallic planar cutting guides, and a second metallic bushing having an outer surface thereof positioned at a second end of each of the first and second metallic planar cutting guides.

Each of the first and second metallic bushings may be embodied as cylindrically-shaped bushings having an elongated bore extending therethrough.

In an embodiment, the second metallic planar cutting guide is spaced apart from the first metallic planar cutting guide in the anterior/posterior direction.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-4, one embodiment of a single use orthopaedic surgical instrument 10 is shown. As its name implies, the single use orthopaedic surgical instrument 10 is intended to be disposed of after use in a single orthopaedic procedure. In the illustrative embodiment described herein, the orthopaedic surgical instrument is embodied as a single use 4-in-1 cutting block 12 for use in the surgical preparation of the patient's distal femur during a knee replacement procedure. As will be discussed below in greater detail, a 4-in-1 cutting block 12 is used to perform four cuts on the patient's distal femur with the same block—an anterior cut, a posterior cut, and two chamfer cuts.

As a single use instrument, the 4-in-1 cutting block 12 may be formed from polymeric materials such as, for example, polyamide, polyphenylsulfone, or polyketone. In such an embodiment, the surfaces used to guide surgical instruments, such as cutting guide surfaces for guiding bone saws and bushings for guiding drills and surgical pins, are formed from a metallic material such as, for example, steel, titanium alloy, or cobalt chromium alloy. Such use of metallic components or "inserts" prevents the surgical tools from coming into contact with the polymeric materials of the block's body.

The metallic components described herein may be secured to the polymer 4-in-1 cutting block in a number of different manners. For example, the metallic components may be overmolded to the polymer cutting block or otherwise secured to it as part of the molding process of the block. The metallic components may also be welded to the cutting block or secured to it with an adhesive. Other methods of securing the metallic components may also be employed.

The 4-in-1 cutting block 12 includes an outer surface 20 and a bone-engaging surface 22 positioned opposite the outer surface 20. The 4-in-1 cutting block 12 has an anterior cutting slot 24 formed near its anterior end 26. The anterior cutting slot 24 is an elongated slot extending in the medial/lateral direction. The anterior cutting slot 24 extends through the entire thickness of the 4-in-1 cutting block 12—that is, the anterior cutting slot 24 extends from the cutting block's outer surface 20 to its bone-engaging surface 22 thereby being open to both surfaces. A metallic anterior cutting guide 28 is secured within the anterior cutting slot 24 of the polymer 4-in-1 cutting block 12. The anterior cutting guide 28 lines the anterior cutting slot 24 and is embodied as a captured cutting guide (i.e., it is closed on all sides so as to capture a saw blade therein), although the cutting block 12 and the cutting guide 28 may alternatively be embodied as a non-captured cutting guide. The anterior cutting guide 28 is sized and shaped to receive the blade (see FIG. 6) of a surgical saw or other cutting instrument and orient the blade to resect the anterior surface of the patient's femur during an orthopaedic surgical procedure.

The 4-in-1 cutting block 12 has a posterior cutting surface 30 formed near its posterior end 32. The posterior cutting surface 30 is an elongated surface extending in the medial/lateral direction. The posterior cutting surface 30 extends the entire thickness of the 4-in-1 cutting block 12—that is, it extends from the cutting block's outer surface 20 to its bone-engaging surface 22. A metallic posterior cutting guide 34 is secured to the posterior cutting surface 30 of the polymer 4-in-1 cutting block 12. The posterior cutting guide 34 is sized and shaped to support and guide the blade (see FIG. 6) of a surgical saw or other cutting instrument and orient the blade to resect the posterior surface of the patient's femur during an orthopaedic surgical procedure. In the illustrative embodiment described herein, the posterior cutting guide 34 is embodied as a non-captured cutting guide, although it may alternatively be embodied as a captured cutting guide.

The 4-in-1 cutting block 12 has an chamfer cutting slot 36 formed near its middle. Specifically, the chamfer cutting slot 36 is located posteriorly of the anterior cutting slot 24 and anteriorly of the posterior cutting surface 30. The chamfer cutting slot 36 is an elongated slot extending in the medial/ lateral direction. The chamfer cutting slot 36 extends through the entire thickness of the 4-in-1 cutting block 12—that is, it extends from the cutting block's outer surface 20 to its bone-engaging surface 22 and, as a result, opens to both surfaces. The chamfer cutting slot 36 is defined by a sidewall 38 of the 4-in-1 cutting block that includes an anterior edge 40 extending in the medial/lateral direction and a posterior edge 42 that is spaced apart from the anterior edge 40 and likewise extends in the medial/lateral direction. The chamfer cutting slot 36 has enlarged rounded medial and lateral ends. In particular the medial edge 44 of the sidewall 38 defining the chamfer cutting slot 36 is cylindrical in shape (i.e., circular when viewed in the front elevation of FIG. 2) and has a diameter that is larger than the A/P width of the slot 36 (i.e., the distance between anterior edge 40 and the posterior edge 42 of the sidewall 38). On the opposite end of the chamfer cutting slot 36, the lateral edge 46 of the sidewall 38 is identical in shape and size. In essence, in the illustrative embodiment described herein, the chamber cutting slot 36 takes on the form of two cylinders spaced at opposite medial and lateral ends connected by a elongated planar slot.

Figure 1:
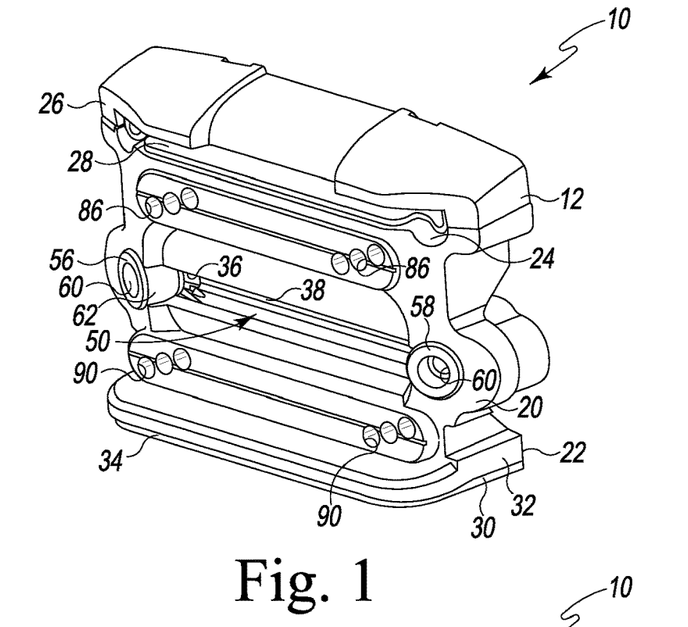
FIG. 1 is a perspective view of an orthopaedic surgical instrument.
Figure 2:
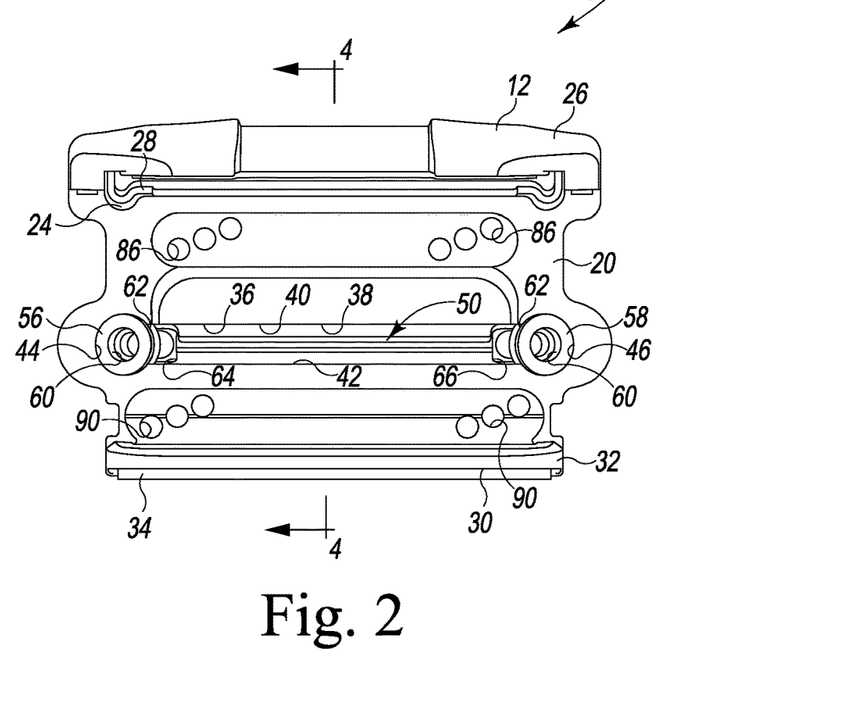
FIG. 2 is an elevation view showing the outer surface of the orthopaedic surgical instrument of FIG. 1.
Figure 3:
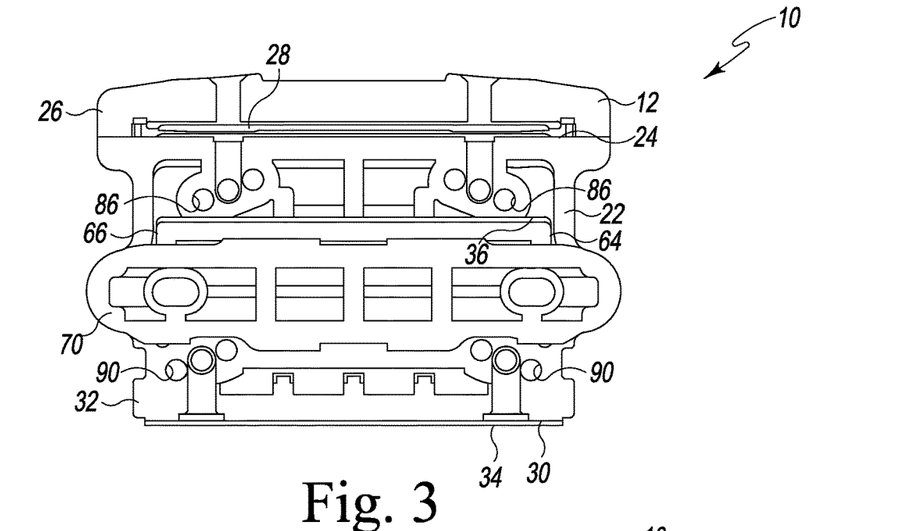
FIG. 3 is an elevation view of the bone-engaging surface of the orthopaedic surgical instrument of FIG. 1.
Figure 4:
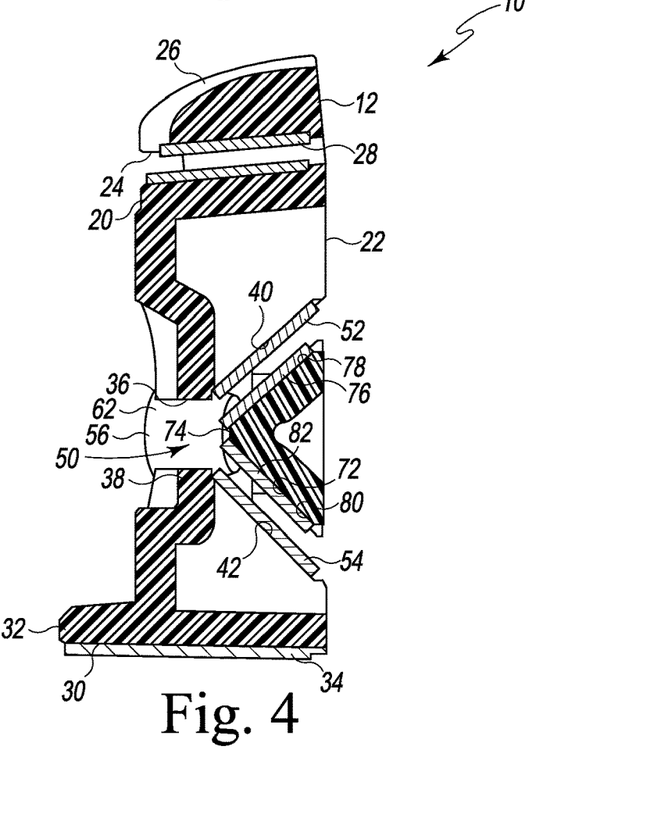
FIG. 4 is a cross section view of the orthopaedic surgical instrument, taken along the line 4-4 of FIG. 2, as viewed in the direction of the arrows.

As can be seen in FIGS. 1, 2, and 4, a metallic captured chamfer cutting guide assembly 50 is positioned in the chamfer cutting slot 36. The chamfer cutting guide assembly 50 includes a metallic planar cutting guide 52 secured to the anterior edge 40 of the sidewall 38 defining the anterior side of the chamfer cutting slot 36, along with a metallic planar cutting guide 54 secured to the posterior edge 42 of the sidewall 38 defining the posterior side of the chamfer cutting slot 36. As can be seen best in FIG. 4, the planar cutting guides 52, 54 are spaced apart from one another in the anterior/posterior direction and are arranged at an oblique angle relative to one another. The longitudinal axis of the planar cutting guides 52, 54 extends in the medial/lateral direction.

The medial and lateral ends of the captured chamfer cutting guide assembly 50 are defined by a pair of metallic bushings 56, 58. In particular, the metallic bushing 56 is positioned in the enlarged cylindrically-shaped medial end of the chamfer cutting slot 36—that is, the metallic bushing 56 is secured in contact with the medial edge 44 of the sidewall 38 defining the medial end of the chamfer cutting slot 36. The metallic bushing 58 is positioned in the enlarged cylindrically-shaped lateral end of the chamfer cutting slot 36—that is, the metallic bushing 58 is secured in contact with the lateral edge 46 of the sidewall 38 defining the lateral end of the chamfer cutting slot 36.

The metallic bushings 56, 58 are cylindrically-shaped and have an elongated bore 60 extending therethrough. The elongated bore 60 is sized to receive a fixation or guide pin for pinning the 4-in-1 cutting block to the patient's distal femur (see FIG. 7), and, optionally, a drill such that the patient's femur may be pre-drilled prior to installation of the guide pins if the surgeon so desires. The metallic bushings 56, 58 are identical in shape and include an annularly-shaped outer surface 62. As can be seen in FIG. 2, the outer surface 62 of the metallic bushing 56 is positioned at the medial end 64 of the planar cutting guides 52, 54, with the outer surface 62 of the metallic busing 58 being positioned at the lateral end 66 of the planar cutting guides 52, 54. In the illustrative embodiment described herein, the outer surface 62 of the metallic bushings 56, 58 is slightly spaced apart from the respective medial end 64 and lateral end 66 of the planar cutting guides 52, 54 (i.e., the bushings 56, 58 are not positioned in contact with the planar cutting guides 52, 54). Such spacing allows for capture of the blade of a bone saw, while also providing for relief from overly tight tolerances in the manufacturing process. However, in another illustrative embodiment, the metallic bushings 56, 58 are positioned in contact with the respective medial end 64 and lateral end 66 of the planar cutting guides 52, 54.

As can be seen best in FIGS. 1 and 4, the 4-in-1 cutting block 12 has a wedge component 70 secured to its bone-engaging surface 22. Like the 4-in-1 cutting block 12, the wedge component 70 is formed from polymeric materials. The wedge component 70 has a wedge-shaped cutting surface 72. The "leading" edge 74 of the wedge-shaped cutting surface 72 extends into the chamfer cutting slot 36. A metallic planar cutting guide 76 is secured to the anterior surface 78 of the wedge-shaped cutting surface 72, with a metallic planar cutting guide 80 being secured to the posterior surface 82 of the wedge-shaped cutting surface 72. Like the cutting guides 52, 54, the planar cutting guides 76, 80 are spaced apart from one another and are arranged at an oblique angle relative to one another. The longitudinal axis of the planar cutting guides 76, 80 extends in the medial/lateral direction. As can be seen in FIG. 4, the cutting guide 76 is spaced apart from, and parallel to, the cutting guide 52, with the cutting guide 80 being spaced apart from, and parallel to, the cutting guide 54. In such a way, the cutting guides 52, 76 cooperate to guide a saw blade during performance of the anterior chamfer cut, with the cutting guides 54, 80 cooperating to guide the saw blade during performance of the posterior chamfer cut (see FIG. 7).

Like the planar cutting guides 52, 54, the outer surface 62 of the metallic bushing 56 is positioned at the medial end of the planar cutting guides 76, 80, with the outer surface 62 of the metallic busing 58 being positioned at the lateral end of the planar cutting guides 76, 80. In the illustrative embodiment described herein, the outer surface 62 of the metallic bushings 56, 58 is slightly spaced apart from the respective medial end and lateral end of the planar cutting guides 76, 80 (i.e., the bushings 56, 58 are not positioned in contact with the planar cutting guides 76, 80). Such spacing allows for capture of the blade of a bone saw, while also providing for relief from overly tight tolerances in the manufacturing process. However, in another illustrative embodiment, the metallic bushings 56, 58 are positioned in contact with the respective medial end and lateral end of the planar cutting guides 76, 80.

Figure 6:
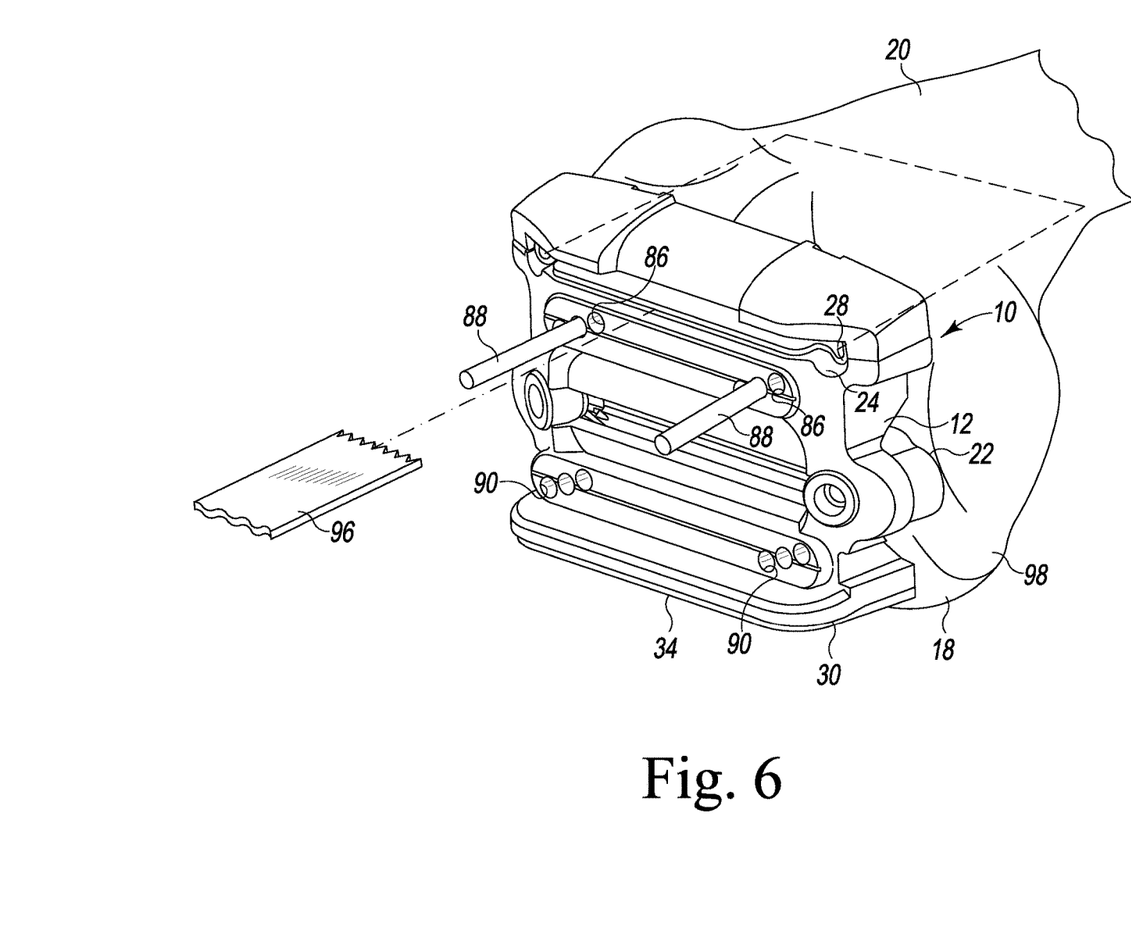
FIG. 6 is a view similar to FIG. 5, but showing the orthopaedic surgical instrument of FIG. 1 being used to perform the anterior and posterior cuts on the distal end of the patient's femur.

The 4-in-1 cutting block 12 has a plurality of guide holes 86 defined therein that are sized to receive a pair of fixation or guide pins 88 (see FIG. 6). The holes 86 are positioned between the anterior cutting slot 24 and the chamfer cutting slot 36 and extend between the outer surface 20 and the bone-engaging surface 22 of the cutting block 12. The holes 86 are arranged in a staggered pattern to permit the surgeon to change the position of the cutting block 12 on the patient's femur without having to remove the fixation pins 88, as described in greater detail below.

The 4-in-1 cutting block 12 also includes another plurality of guide holes 90 positioned between the chamfer cutting 36 and the posterior cutting surface 30. Each guide hole 90 is sized to receive one of the fixation pins 88 in a similar manner to the guide holes 86 and thereby extends between the outer surface 20 and the bone-engaging surface 22 of the cutting block 12. Like the guide holes 86, the guide holes 90 are arranged in a staggered pattern to permit the surgeon to change the position of the cutting block 12 on the patient's femur without having to remove the fixation pins 88.

In operation, the surgeon may utilize the orthopaedic surgical instrument 10 to prepare the distal end 18 of the patient's femur 20 to receive a prosthetic femoral component. To do so, the surgeon may secure the 4-in-1 cutting block 12 to the patient's femur 20 and thereafter use the metallic cutting guides of the cutting block 12 to guide a cutting saw blade in making a series of four resections of the distal end 18 of the patient's femur 20.

Figure 5:
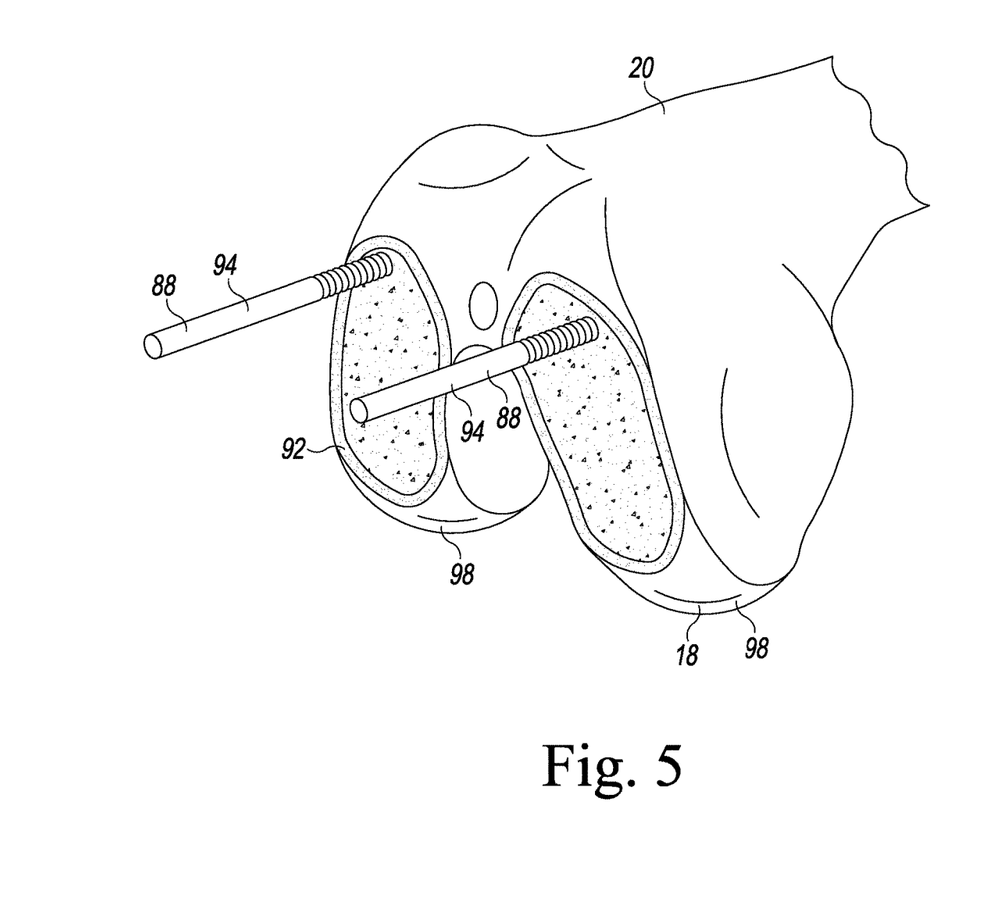
FIG. 5 is a perspective view showing a pair of fixation pins secured to a distal end of a patient's femur.

During an orthopaedic surgical procedure, the surgeon may first resect the distal end 18 of the patient's femur 20 to create a surgically-prepared distal surface 92. The surgeon may then secure a pair of fixation pins 88 to the surgically-prepared distal surface 92 of the patient's femur 20, as shown in FIG. 5. To do so, the surgeon may size the patient's femur 20 for the prosthetic femoral component and set the femoral rotation. One exemplary procedure for locating fixation pins during a femoral sizing and rotation setting procedure is described in the SIGMA® Fixed Reference Surgical Technique by DePuy Orthopaedics, Inc. (2010), which is expressly incorporated herein by reference. After sizing the femoral component and setting the rotation, the surgeon may attach the fixation pins 88 to the surgically-prepared distal surface 92 of the patient's femur 20.

After attaching the fixation pins 88, the surgeon may position the 4-in-1 cutting block 12 on the surgically-prepared distal surface 92 of the patient's femur 20. To do so, the surgeon may align the shafts 94 of the fixation pins 88 with a pair of the guide holes 86 of the 4-in-1 cutting block 12. The surgeon may then advance the 4-in-1 cutting block 12 over the shafts 94 in a direction toward the surgically-prepared distal surface 92 of the patient's femur 20. The bone-engaging surface 22 of the 4-in-1 cutting block 12 contacts the surgically-prepared distal surface 92 when the instrument 10 is positioned on the distal end 18 of the patient's femur 20, as shown in FIG. 6. If the surgeon desires to relocate the 4-in-1 cutting block 12, the surgeon may utilize another combination of guide holes 86 to change the position of the cutting block 12 on the patient's femur 20. If additional fixation is necessary, the surgeon may insert additional fixation pins 88 through the guide holes 90 defined in the 4-in-1 cutting block 12.

Once installed in such a manner, the surgeon may use the 4-in-1 cutting block 12 to make a number of resections of the distal end 18 of the patient's femur 20. For example, as shown in FIG. 6, the anterior cutting guide 28 defines a resection plane that extends through the distal end 18 of the patient's femur 20. The surgeon may advance a cutting tool, such as, for example, a surgical cutting saw 96 through the anterior cutting guide 28 to engage the patient's femur 20 and operate the surgical saw 96 to surgically prepare an anterior surface of the patient's femur 20 to receive the prosthetic femoral component. The surgeon may similarly use the posterior cutting guide 34 to resect the posterior condyles 98 of the patient's femur 20 and surgically prepare the posterior surfaces of the patient's femur 20 to receive the prosthetic femoral component.

Figure 7:
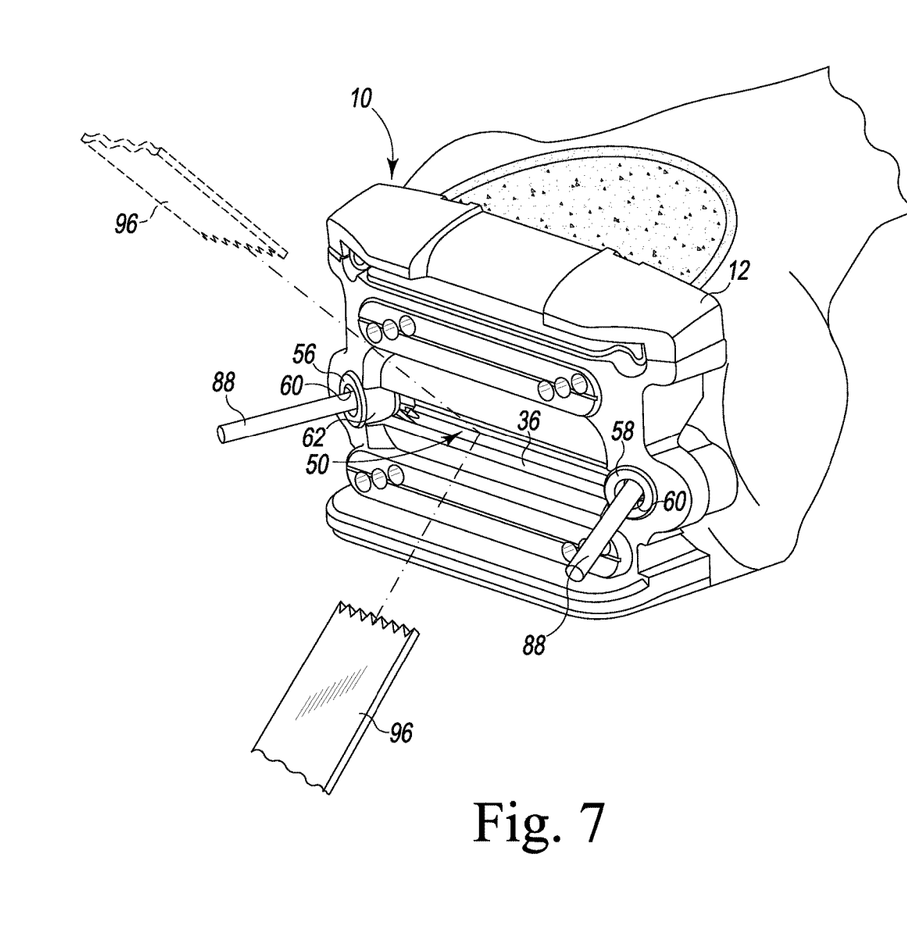
FIG. 7 is a view similar to FIG. 6, but showing the orthopaedic surgical instrument of FIG. 1 being used to perform the chamfer cuts on the distal end of the patient's femur.

As shown in FIG. 7, the surgeon may also use the captured chamfer cutting guide assembly 50 in cooperation with the planar cutting guides 76, 80 of the wedge component 70 to make chamfer cuts on the patient's femur 20. To do so, the surgeon may first insert fixation pins 88 through the elongated bores 60 of the metallic bushings 56, 58 of the chamfer cutting guides assembly 50. The surgeon may then remove any fixation pins 88 from the guide holes 86, 90 since fixation pins 88 positioned in the guide holes 86, 90 would disrupt the chamfer cutting process. The surgeon may then advance the surgical cutting saw 96 through opening between the cutting guides 52, 76 to guide the saw 96 during performance of the anterior chamfer cut (as shown in solid lines in FIG. 7), and thereafter through the opening between the cutting guides 54, 80 to guide the saw 96 during performance of the posterior chamfer cut (as shown in phantom lines in FIG. 7).

During performance of such chamfer cuts, the metallic cutting guides 52, 54 function as a saw stop to prevent the saw 96 from engaging the polymeric body of the 4-in-1 cutting block 12 that defines the anterior and posterior edges of the chamfer cutting slot 36. Similarly, the outer surfaces 62 of the metallic bushings 56, 58 function as a saw stop to prevent the saw from engaging the polymeric body of the of the 4-in-1 cutting block 12 that defines the medial and lateral edges of the chamfer cutting slot 36. Likewise, the wedge component's metallic cutting guides 76, 80 function as a saw stop to prevent the saw 96 from engaging the wedge-shaped cutting surface 72 of the wedge component 12.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, although use of the metallic bushings 56, 58 as saw stops has herein been described in the illustrative example of a 4-in-1 block, it should be appreciated that other orthopaedic instruments may also be embodied with such a concept. For example, other orthopaedic cutting blocks may be so embodied.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument comprising:
a polymer 4-in-1 femoral cutting block having a sidewall that partially defines a chamfer cutting slot having a slot section between a first opening defined in a first surface of the sidewall and a second opening defined in a second surface of the sidewall,
a first metallic planar cutting guide secured within the chamfer cutting slot of the polymer 4-in-1 femoral cutting block,
a second metallic planar cutting guide secured within the chamfer cutting slot of the polymer 4-in-1 femoral cutting block, the second metallic planar cutting guide being arranged at an oblique angle relative to, and spaced apart from, the first metallic planar cutting guide,
a first metallic bushing secured within the chamfer cutting slot of the polymer 4-in-1 femoral cutting block, an outer surface of the first metallic bushing being positioned at a lateral end of each of the first and second metallic planar cutting guides, the first metallic bushing extending along the slot section of the chamfer cutting slot, wherein the first metallic bushing is configured to prevent a blade from engaging the polymer 4-in-1 femoral cutting block, and
a second metallic bushing secured within the chamfer cutting slot of the polymer 4-in-1 femoral cutting block, an outer surface of the second metallic bushing being positioned at a medial end of each of the first and second metallic planar cutting guides, the second metallic bushing extending along the slot section of the chamfer cutting slot, wherein the second metallic bushing is configured to prevent the blade from engaging the polymer 4-in-1 femoral cutting block.

2. The orthopaedic surgical instrument of claim 1, wherein:
the outer surface of the first metallic bushing is spaced apart laterally from the lateral end of each of the first and second metallic planar cutting guides, and
the outer surface of the second metallic bushing is spaced apart medially from the medial end of each of the first and second metallic planar cutting guides.

3. The orthopaedic surgical instrument of claim 1, wherein:
the outer surface of the first metallic bushing contacts the lateral end of each of the first and second metallic planar cutting guides, and
the outer surface of the second metallic bushing contacts the medial end of each of the first and second metallic planar cutting guides.

4. The orthopaedic surgical instrument of claim 1, wherein each of the first and second metallic bushings comprises cylindrically-shaped bushings having an elongated bore extending therethrough.

5. The orthopaedic surgical instrument of claim 1, wherein the second metallic planar cutting guide is spaced apart from the first metallic planar cutting guide in the anterior/posterior direction.

6. The orthopaedic surgical instrument of claim 1, further comprising:
a third metallic planar cutting guide secured within the chamfer cutting slot of the polymer 4-in-1 femoral cutting block, and
a fourth metallic planar cutting guide secured within the chamfer cutting slot of the polymer 4-in-1 femoral cutting block, the fourth metallic planar cutting guide being arranged at an oblique angle relative to the third metallic planar cutting guide.

7. The orthopaedic surgical instrument of claim 1, wherein the polymer 4-in-1 femoral cutting block further has an anterior cutting slot defined therein, the anterior cutting slot being spaced apart anteriorly from the chamfer cutting slot, further comprising a metallic anterior cutting guide secured within the anterior cutting slot of the polymer 4-in-1 femoral cutting block.

8. The orthopaedic surgical instrument of claim 7, wherein the polymer 4-in-1 femoral cutting block further has a posterior cut surface defined therein, the posterior cut surface being spaced apart posteriorly from the chamfer cutting slot, further comprising a metallic posterior cutting guide secured to the posterior cut surface of the polymer 4-in-1 femoral cutting block.

9. An orthopaedic surgical instrument comprising:
a polymer 4-in-1 femoral cutting block having an inner sidewall that partially defines a chamfer cutting slot, the chamfer cutting slot having a medial end and a lateral end, and
a metallic captured chamfer cutting guide assembly secured within the chamfer cutting slot, the metallic captured chamfer cutting guide assembly comprising: (i) a first metallic planar cutting guide, (ii) a second metallic planar cutting guide arranged at an oblique angle relative to, and spaced apart from, the first metallic planar cutting guide, (iii) a first metallic bushing having an outer surface thereof positioned at a lateral end of each of the first and second metallic planar cutting guides, the first metallic bushing being positioned inside the chamfer cutting slot at the lateral end abutting the inner sidewall, and (iv) a second metallic bushing having an outer surface thereof positioned at a medial end of each of the first and second metallic planar cutting guides, the second metallic bushing being positioned inside the chamfer cutting slot at the medial end abutting the inner sidewall.

10. The orthopaedic surgical instrument of claim 9, wherein:
the outer surface of the first metallic bushing is spaced apart laterally from the lateral end of each of the first and second metallic planar cutting guides, and
the outer surface of the second metallic bushing is spaced apart medially from the medial end of each of the first and second metallic planar cutting guides.

11. The orthopaedic surgical instrument of claim 9, wherein:
the outer surface of the first metallic bushing contacts the lateral end of each of the first and second metallic planar cutting guides, and
the outer surface of the second metallic bushing contacts the medial end of each of the first and second metallic planar cutting guides.

12. The orthopaedic surgical instrument of claim 9, wherein each of the first and second metallic bushings comprises cylindrically-shaped bushings having an elongated bore extending therethrough.

13. The orthopaedic surgical instrument of claim 9, wherein the second metallic planar cutting guide is spaced apart from the first metallic planar cutting guide in the anterior/posterior direction.

14. The orthopaedic surgical instrument of claim 9, further comprising:
a third metallic planar cutting guide secured within the chamfer cutting slot of the polymer 4-in-1 femoral cutting block, and
a fourth metallic planar cutting guide secured within the chamfer cutting slot of the polymer 4-in-1 femoral cutting block, the fourth metallic planar cutting guide being arranged at an oblique angle relative to the third metallic planar cutting guide.

15. The orthopaedic surgical instrument of claim 9, wherein the polymer 4-in-1 femoral cutting block further has an anterior cutting slot defined therein, the anterior cutting slot being spaced apart anteriorly from the chamfer cutting slot, further comprising a metallic anterior cutting guide secured within the anterior cutting slot of the polymer 4-in-1 femoral cutting block.

16. The orthopaedic surgical instrument of claim 15, wherein the polymer 4-in-1 femoral cutting block further has a posterior cut surface defined therein, the posterior cut surface being spaced apart posteriorly from the chamfer cutting slot, further comprising a metallic posterior cutting guide secured to the posterior cut surface of the polymer 4-in-1 femoral cutting block.

17. An orthopaedic surgical instrument comprising:
a polymer cutting block having a cutting slot defined therein, the cutting slot having a straight section extending between a medial end and a lateral end, and
a metallic captured cutting guide assembly secured within the cutting slot, the captured metallic chamfer cutting guide assembly comprising: (i) a first metallic planar cutting guide, (ii) a second metallic planar cutting guide spaced apart from the first metallic planar cutting guide, (iii) a first metallic bushing having an outer surface thereof positioned at a first end of each of the first and second metallic planar cutting guides, the first metallic bushing positioned at the medial end of the cutting slot between the polymer cutting block and the straight section of the cutting slot, and (iv) a second metallic bushing having an outer surface thereof positioned at a second end of each of the first and second metallic planar cutting guides, the second metallic bushing positioned at the lateral end of the cutting slot between the polymer cutting block and the straight section of the cutting slot.

18. The orthopaedic surgical instrument of claim 17, wherein each of the first and second metallic bushings comprises cylindrically-shaped bushings having an elongated bore extending therethrough.

19. The orthopaedic surgical instrument of claim 17, wherein the second metallic planar cutting guide is spaced apart from the first metallic planar cutting guide in the anterior/posterior direction.

* * * * *